United States Patent [19]

Santus et al.

[11] Patent Number: 5,460,828

[45] Date of Patent: Oct. 24, 1995

[54] PROCESS FOR THE PREPARATION OF MICROGRANULES SUITABLE FOR SUSPENSION IN FLUIDS

[75] Inventors: Giancarlo Santus, Milan; Guiseppe Bottoni, Bergamo; Roberto Golzi, Cremona, all of Italy

[73] Assignee: Recordati S.A., Chemical and Pharmaceutical Company, Chiasso, Switzerland

[21] Appl. No.: 188,193

[22] Filed: Jan. 28, 1994

[30] Foreign Application Priority Data

Jan. 28, 1993 [IT] Italy .................................. MI9300136

[51] Int. Cl.⁶ ........................................................ A61K 9/14
[52] U.S. Cl. ........................... 424/489; 424/490; 424/470
[58] Field of Search .................................... 424/489, 490, 424/491, 409

[56] References Cited

U.S. PATENT DOCUMENTS

| | | | |
|---|---|---|---|
| 4,886,669 | 12/1989 | Ventouras | 424/469 |
| 4,948,589 | 8/1990 | Ilijima et al. | 424/490 |
| 5,043,167 | 8/1991 | Rotini et al. | 424/490 |
| 5,296,236 | 3/1994 | Santus et al. | 424/490 |

FOREIGN PATENT DOCUMENTS

| | | |
|---|---|---|
| 2900154.7 | 5/1990 | Germany . |
| 2204792 | 5/1988 | United Kingdom . |

OTHER PUBLICATIONS

Gaillard, C. et al., *Eur. J. Pharm. Biopharm.* 38(5):163–168, 1992.
Database WPI, Abstract, AN 88–326816 & JP–A–63 240 934, (Taisho Pharmaceut KK) Oct. 6, 1988.
Database WPI, Abstract, AN 76–83997X & JP–A–51 106 712, (Takeda Chemical IND KK) Sep. 22, 1976.

*Primary Examiner*—Thurman K. Page
*Assistant Examiner*—William E. Benston, Jr.
*Attorney, Agent, or Firm*—Darby & Darby

[57] ABSTRACT

The object of the invention is a process for the preparation of microgranules to be used in controlled-release liquid pharmaceutical compositions. Operating with high-shear mixer-granulators within clearly established crucial parameter ranges, this process results in microgranules having a particle size distribution, a density, a surface and a shape which make them particularly suitable for coating and then suspension in fluids.

13 Claims, 2 Drawing Sheets

PROCESS FOR THE PREPARATION OF MICROGRANULES SUITABLE FOR SUSPENSION IN FLUIDS

FIELD OF THE INVENTION

This invention involves a granulation process to obtain microgranules for use in pharmaceutical compositions. Said microgranules have a limited size distribution and morphological characteristics that ensure both uniform coating and easy suspension after coating, even in low-density aqueous vehicles.

BACKGROUND OF THE INVENTION

The technology to produce granulates from powder mixtures has long been known in pharmaceutics. For purposes of administration, these granulates are usually converted into tablets, enclosed in capsules or in sachets.

It has also been long known that granules or tablets can be coated with films, which can serve to delay the release of the active ingredient they contain, disguise an unpleasant taste, and/or improve the stability of the composition.

A major limitation of the use of such coated granulates in liquid formulations is that it has been difficult to obtain particles of an appropriate size to enable them to be easily suspended and kept in suspension in the fluid vehicle.

Particles of a size larger than about 500 μm tend to settle rapidly, resulting in a non-homogeneous distribution of the product within the vehicle. It is instead essential that the suspension remain homogeneous, after a slight stirring, for the time required to guarantee a consistent administration. It is also preferable to avoid the unpleasant sensation that one may have when ingesting a suspension containing a coarse solid particulate (sand effect).

These requirements may generally be fulfilled by reducing the size of the microgranules to be suspended so that they do not exceed 500 μm. However, the commonly known technologies described below can not be readily applied to obtain final granules of this size range.

One of the most commonly used technologies involves depositing the active ingredient on inert spherical-shaped particles called "cores", which are available on the market in different sizes but which are unlikely to result in microgranules of a diameter smaller than 500 μm.

After sequential deposition on an inert core of the active ingredient, the binder and the subsequent polymer coatings, the final granule size is unlikely to be smaller than 800–1000 μm. Even using 250 μm (60 mesh) saccharose crystals as inert cores, the quantity of material to be deposited is such that final particles of sizes smaller than 500–800 μm are difficult, if not impossible, to obtain. The final granulate forms resulting from this process are therefore totally unsuitable for inclusion in liquid dosage.

The known coating techniques for crystals or granules which are generally meant to disguise the taste of the active ingredient, to control release, or to give stability to the product, can in theory be applied to particles smaller than 500 μm. Generally, however, they require specific processes such as microencapsulation by coacervation or interface polymerization. These methods have a number of serious drawbacks, including a requirement for excessive quantities of solvents used, the high cost of solvent recovery, and the difficulties inherent in a more complex production technology.

Although film-coating can be used to coat crystalline particles of a size smaller than 300 μm, an important requirement is that the particles be as much as possible identical one to the other in size and shape.

During the filming process, very small particles tend to adhere to one another, forming agglomerates that would adversely affect the consistency and reproducibility of the active ingredient release profile.

Furthermore, the problems caused by agglomeration tend to become worse as treated product volumes increase. In addition, it is difficult to ensure consistent coating characteristics, as the very dispersed particle-size distribution and the non-homogeneous particle shapes cause very variable surface areas. This leads to a correspondingly variable quantity of deposited coating per unit surface area, leading ultimately to a non-homogeneous release of the active ingredient.

The crystalline form and the density of the material being processed are important factors in the coating of crystals. Needle-shaped crystals can be coated with extreme difficulty, using special precautions; inevitably, resulting coating is distributed in a non-homogeneous way on the core surface and is thinner at the crystal edges. Cuboidal crystals are easier to coat, but also present problems related to the presence of edges. In addition, it is necessary for the density of the crystals to be such that the above-mentioned agglomeration and adhesion problems can be avoided.

Since crystal shape and density are characteristic of the crystalline form itself, it is evident that such properties cannot be readily modulated to suit the requirements of the filming process.

The choice of the equipment also has some influence on microgranulate preparation. The equipment generally used includes: fluid-bed granulators, conventional mixers, spheroidal-shaping extruders and fast mixers.

In a fluid-bed apparatus the powder is kept in suspension by an appropriate air flow, while the granulation fluid is simultaneously sprayed. The resulting product has an even shape, but is very porous and has a low density. The granulate is therefore unsuitable for subsequent coating, as it is inclined to break with a change in surface area and does not exhibit a uniform film/surface unit ratio. Furthermore, the material to be subjected to a fluid-bed coating process must be made up of particles of sufficient density to avoid the agglomeration phenomenon described. Otherwise, the particles tend to occupy the upper section of the apparatus, are not subject to the normal movement inside the apparatus, and thus do not receive an appropriate gradual coating.

A conventional mixer-granulator consists of a vessel, which may be of varying shape, equipped with an agitator that keeps the powder moving while the granulation fluid is being added. The motion is slow and the resulting granulate, even though suitable for making conventional dosage forms such as tablets or capsules, does not possess the density, shape and particle-size distribution suitable for subsequent coating.

Unlike conventional mixer-granulators, extruder-spheronizers can produce spherical particles of homogeneous sizes and even shapes and surfaces. The limitation that prevents their application to microgranulates suitable for liquid suspensions is the average product size, which is rarely smaller than 1–2 mm and in any case never smaller than 500 μm.

A high-shear mixer-granulator is made up of a vessel in which the mixture to be granulated is introduced that is equipped with a mixer and a mill that rotate with a normal mixer motion. Since the mixer and the mill have variable and adjustable speeds, they ensure densification and preparation of the granulate in shorter times as compared to conventional granulators.

It has now been found that, using high-shear mixer-granulators and operating within specific critical ranges of the parameters that control the granulation process, it is possible to obtain a microgranulate of a size smaller than 500 μm. It is an object of the present invention to provide a size distribution, density, surface and shape of the particles produced that makes them particularly suitable for coating and for suspension in low density fluids.

SUMMARY OF THE INVENTION

The present invention teaches a process for the preparation of microgranules suitable for use in controlled-release pharmaceutical preparations, said microgranules having a size smaller than 500 μm, a spheroidal shape and a surface suitable for coating. The process of the present invention is carried out in a fast mixer equipped with a mixer and a mill, by mixing the active ingredient with appropriate excipients (said active ingredient and excipients being referred to as "the powders"), wetting the mixture by spraying with a granulation fluid of defined flow rates and pressures, and kneading the mixture for a defined time using specific mixer and mill speeds.

In another aspect, the present invention defines the characteristics of microgranules that indicate their suitability for coating and use in liquid suspension formulations.

In still another aspect, the present invention provides microgranules comprising a wide variety of pharmaceutical agents whose particular solubility properties and controlled-release requirements can be accommodated by the process of the present invention.

DETAILED DESCRIPTION OF THE INVENTION

Figure 1:
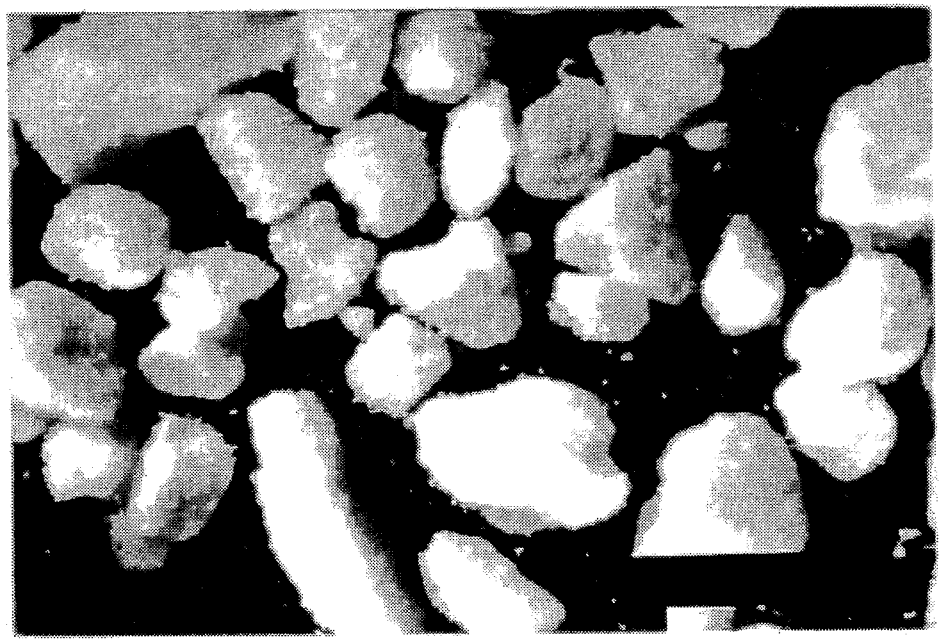
FIG. 1 shows a stereomicroscope image of microgranules of uneven shapes and surfaces, corresponding to preparation A in Example 1. (Magnification=33X).

The microgranulate preparation process can be summarized as follows:

dry-mixing the powders inside a high-shear mixer-granulator, wetting the mixture by spraying with a granulation fluid at a set flow rate, (preferably by atomizing so as to ensure a more homogeneous dispersion of the granulation fluid while the product is subject to the combined actions of the mixer and the mill), kneading for a fixed time after wetting, by the combined mixer and mill actions, drying to a residual humidity of 1–10%, preferably 5–8%, and sieving for selection of the required particle size.

Important process parameters that affect the finished product characteristics include: (1) quantity of granulation fluid, (2) fluid addition rate, (3) kneading time, (4) atomizing pressure, and (5) mixer and mill rotating speeds during wetting and kneading.

Specific combinations and acceptable and preferred ranges of these parameters as described below are also objects of this invention and result in a product that has the required size and the most suitable characteristics for a subsequent coating process.

Table 1 shows the maximum range for each parameter within which it is possible to obtain the required product (column I) and the preferred range which produces an optimum quality product (column II):

TABLE 1

| Process parameters | I | II |
|---|---|---|
| Fluid (g/Kg of product) | 80–180 | 100–150 |
| Spray rate (g/min) | 10–40 | 20–30 |
| Kneading time (min) | 5–15 | 8–12 |
| Spray pressure (bars) | 1.5–2.5 | 2 |
| Mixer speed (rpm) | 175–350 | 175–350 |
| Mill speed (rpm) | 2000–4000 | 2000–4000 |

The active ingredients suitable for formulation into microgranules include any solid pharmaceutical substance suitable for oral administration. Nonlimiting examples include:

analgesics such as acetaminophen, phenacetin, sodium salicilate;

antitussives such as dextromethorphan, pholcodine, isoaminile, codeine phosphate, moguisteine;

bronchodilators such as diprophylline, albuterol, procaterol;

antipsychotics such as droperidol, haloperidol, oxypertine, perycyazine, chlorpromazine;

selective β2 agonists such as salbutamol, orciprenaline sulphate, pirbuterol, terbutaline, ephedrine, tolbuterol;

calcium channel blockers such as nifedipine, nicardipine, diltiazem, verapamil, lercanidipine;

antiparkinson drugs such as benzhexol, biperiden, norphenadrine, procyclidine, pergolide;

NSAIDs such as aspirin, ketoprofen, indomethacin, ibuprofen, diclofenac sodium, piroxicam, naproxen, ketorolac;

antihistamines such as brompheniranine, cholrpheniramine, cyproheptadine, pheniramine, mebhydrolin, trimeprazine, triprolidine, acrivastine, terfenadine, clemastine, dimethindene;

antiemetics such as prochlorperazine, domperidone, cyclizine, ondansetron, triethyl perazine;

antidiarrheal drugs such as loperamide, sulphasalazine;

anxiolytics such as chlordiazepoxide, oxazepam, medazepam, alprazolam, clonazepam, lorazepam;

oral antidiabetic drugs such as gliquidone, gliclazide;

opioid analgesics such as dextromoramide, morphine, dihydrocodeine, methadone, dipipanone, phenazocine;

motility stimulants such as cisapride;

diuretics such as bumetanide, bendrofluazide, hydrochlorothiazide, mefruside, merthylclothiazide, xipamide, furosemide, ethacrynic acid;

nitrates such as isosorbide dinitrate;

β-blockers such as propranolol;

antispasmodics such as hyoscine butylbromide, poldine methylsulphate, dicyclomine, pipenzolate, propanthelin, flavoxate, terflavoxate;

peripheral vasodilators such as cinnarizine, thymoxamine;

lipid lowering drugs such as fenofibrate;

antidepressants such as protriptyline, iprindole, trazodone, clomipramine, fluexetine, citalopram, amitriptyline;

laxatives such as bisacodyl, danthron;

4-quinolones such as nalidixic acid;

vitamins such as pyridoxine;

antiasthmatic drugs: such as theophylline, aminophylline;

antiepileptic drugs such as valproate, carbamazepine, phenytoin;

and their pharmaceutically acceptable salts.

The materials (other than the pharmaceutical itself) that can be used in making the base granulate are any of those commonly used in pharmaceutics and should be chosen on the basis of compatibility with the active ingredient. For instance, the excipient or excipients used can be chosen from those commonly used in a wet mixture, that is:

lubricants such as talc or magnesium stearate;

binders such as polyvinylpyrrolidone, polyvinylpyrrolidone /vinyl acetate copolymer or cellulose derivatives such as for instance methyl cellulose, carboxymethyl cellulose and the like;

fillers such as dibasic calcium phosphate, lactose, microcrystalline cellulose, starch, sugar, glucose or high molecular weight hydrogenated vegetable oils.

The choice of the excipients to be used in combination with a given active ingredient should take into account the physico-chemical properties of the active ingredient; this is particularly important when the active ingredient comprises more than 60% of the total weight of the granulate.

As a nonlimiting example, with a highly soluble active ingredient it may be desirable to use excipients that are insoluble, swell or have hydrophobic characteristics. This limits the diffusion of the active ingredient from the microgranular core, and obviates the need to apply excessive film quantities in order to control release. In this case, the choice of the excipients may be confined to calcium phosphate, hydrogenated vegetable oil, starch and cellulose derivatives.

On the other hand, with poorly soluble active ingredient it is important to aid dissolution and avoid a situation in which the granulate core itself interferes with the function of the coating to modulate release. To this end, highly soluble excipients such as sucrose can be useful. In summary, the choice of the excipients is important but it depends on the physicochemical properties of the active ingredient and it is impossible to give generally applicable guidelines therefor. The choice of the excipients is outside the scope of the invention.

The choice of the binder (e.g., polyvinylpyrrolidone, polyvinylpyrrolidone/vinylacetate or any mixtures thereof) depends on the friability of the finished granule. If the granule is friable, it may break during coating, causing a change in the surface area values and a consequent change in the ratio between applied film and unit surface.

The granulation fluid can be water or organic solvents such as, for instance, ethyl alcohol or other commonly used solvents, or mixtures of water and solvents.

To determine that a suitable granulate has been obtained, the following characteristics of the granulated product are monitored:

Particle Size Distribution

Particle size distribution is determined by sieving (Advances in Pharmaceutical Sciences; Vol. 2, page 95–174, 1967; Acad. Press Ed.-New York). The granulate is placed over a set of sieves with meshes of decreasing size placed one over the other and subjected to vibration for the time necessary to obtain a consistent value for the size distribution. In most cases, a sieving time of 5 to 10 minutes is sufficient. At the end of the procedure, the quantity of granules left in each sieve is determined by weight.

By plotting the logarithm of the average mesh against the percent frequency of the oversize cumulative weight, a line is obtained that represents the particle size distribution. From this plot, using standard statistical techniques, it is possible to obtain the value of:

1) The Mean Geometric Diameter ($d_g$), which is the diameter corresponding to 50% of the sieved particles; and 2) The Geometric Standard Deviation ($\sigma_g$) which is the measure of how much the granule size deviates from $d_g$ and is the ratio between the diameter corresponding to 15.87% of the particles and $d_g$.

In an acceptable preparation, more than 85% of the granules have a size between about 90 and about 300 µm; a preferred size distribution is one in which 85% of the granules have a size between about 125 and about 300 µm.

Density

The following density measures were evaluated for granulate characterization (Advances in Pharmaceutical Sciences; Vol. 2, pages 181–220, 1967; Acad. Press Ed.-New York):

1) Aerated Density is the ratio between the powder mass and the volume of the bed poured into a graduated container.

2) Packed Density is the ratio between the powder mass and the volume occupied by the powder bed after a standard number of vibrations and followed by settling.

3) Apparent Density is the ratio between the powder mass and volume filled by the powder mass excluding superficial porosities. This value is determined by calculating the difference between the volume filled by a solvent in an empty graduated vessel and the volume of solvent displaced by the sample introduced into the same vessel. The ratio between the sample mass and the difference between the volumes is the apparent density value. This parameter is relevant to a determination of surface area. See, infra.

Carr Index (Compressibility Percentage).

This index is an indirect measure of the granulate flowability. It is determined by the ratio:

packed density−aerated density/packed density*100

(Pharmaceutical Preformulation; pages 209–214, 1988; Ellis Horwood Ed.-Chichester, England). The relationship between the Carr Index and flowability is given in Table 2. The flowability grading follows selection criteria that are stricter than those normally adopted for granulate evaluation, precisely in consideration of the particular requirements of the product obtained by the invention.

TABLE 2

| CARR INDEX (%) | Flowability |
| --- | --- |
| 5–10 | Good |
| 11–15 | Adequate |

TABLE 2-continued

| CARR INDEX (%) | Flowability |
| --- | --- |
| 16–21 | Inadequate |

Angle of repose

Together with microscopic observation, the angle of repose provides information on the product shape. The powder is dropped from a standard funnel onto a surface, forming a cone, and the base angle of the cone is measured. The smaller the cone base angle, the more even the shape of the particle (Pharmaceutical Preformulation; pages 209–214, 1988; Ellis Horwood Ed.-Chichester, England)

The relationship between angle of repose and flowability is given in Table 3.

TABLE 3

| Angle of Repose (°) | Flowability |
| --- | --- |
| <25 | Excellent |
| 25–30 | Good |
| 30–40 | Acceptable |
| >40 | Poor |

Evaluation of Properties of a Microgranulate Suitable for Coating

Taken together, the above-described parameters determine if a particular microgranulate preparation is suitable for a subsequent coating process. The acceptable and preferred values that define a suitable preparation are described in Table 4.

TABLE 4

| Characteristics | Acceptable | Preferred |
| --- | --- | --- |
| Mean geom. diameter ($d_g$) (μm) | 120–200 | 130–170 |
| Standard deviation ($\sigma_g$) | 1.4–2.0 | 1.5–1.8 |
| Aerated density (g/ml) | 0.4–0.7 | 0.50–0.66 |
| Packed density (g/ml) | 0.5–0.9 | 0.55–0.80 |
| Apparant density (g/ml) | 1.2–1.5 | 1.30–1.45 |
| Carr index (%) | 5–15 | 6–12 |
| Angle of repose (°) | 20–40 | 26–30 |

The observations of shape and surface made by electron microscopy and stereomicroscopy are also taken into account. A spheroidal shape and a smooth surface substantially free of roughness are directly correlated to granule flowability and are quantified with the above Carr Index and Angle of Repose values.

Testing of Suitability for Coating

Once it is established that a particular microgranulate preparation has the desired characteristics for coating, its suitability is measured directly by sequentially depositing on the granules equal quantities of two different coatings, followed by evaluation of the controlled-release properties of the active ingredients.

First, to determine the amount of coating to be applied, it is necessary to calculate the surface area (SA) of each preparation. For spherical particles, the unit surface area can be calculated according to the formula:

$$SA = 6/AD \cdot d_{vs},$$

where AD=apparent density and $d_{vs}$=geometric diameter volume surface.

$d_{vs}$ is obtained from the values of $d_g$ and $\sigma_g$ using the formula:

$$\log d_{vs} = \log d_g - 1.151 \log^2 \sigma_g.$$

The apparent density is used to calculate SA, since this measure more than any accounts for surface porosity, a factor of major interest when considering the actual surface to be coated (Drug Development and Industrial Pharmacy, 14 (4), 573 (1988)). It will be understood to those skilled in the art that the foregoing calculation yields approximate values for surface area since the calculation assumes that the particles are spherical. Nevertheless, the obtained values are adequate for purposes of the invention.

Once an appropriate amount of coating per unit surface area has been identified (for a given microgranule formulation containing a given active ingredient) the total coating quantity to be applied to the same type of microgranule formulation can be calculated from the SA value. The total surface area to be coated is obtained by multiplying the SA value by the total granulate weight in grams. This permits the same quantity of coating to be deposited in different batches of microgranules which ensures a consistently reproducible release profile from batch to batch.

There is an inverse relationship between the film amount and the active ingredient dissolution rate. The dissolution rate, however, should be determined case by case, since, for each single active ingredient, it depends both on the particular granulate and on the type of coating used.

The first coating, laid directly on the granule, is suitable for controlling the release of the active ingredient. The second coating, laid on the first coating, has the function of aiding contact with the dissolution vehicle and has hydrophilic characteristics. Typically, the first coating may comprise ethyl cellulose mixed with plasticizers, and the second coating may comprise cellulose acetate phthalate mixed with plasticizers. However, any coating means with the appropriate lipophilic or hydrophilic characteristics can be used.

In the present invention, it is not necessary and most often it is not desirable that the uncoated microgranules possess any controlled release properties. An exception to this, as stated above, is when the active ingredient is highly soluble in which case it may be desirable to limit the rate of diffusion of the active ingredient from the core. In most cases, the first coating is primarily or exclusively responsible for controlling release. The quantity of this coating applied to the different granulates should therefore take into account the intrinsic solubility of the active ingredient. Assuming the granule core sizes are equal, the more soluble the active ingredient, the thicker the coating required for controlling release. Optimization of the coating thickness is within the skill in the art requiring only routine experimentation.

The coating requirements have been compared for granules having identical shape, size and surface area but containing active ingredients with different characteristics. As illustrated in Table 5, different relative amounts of the first coating need to be applied in order to obtain comparable release profiles.

TABLE 5

| | Diprophylline | Acetaminophen | Ibuprofen |
| --- | --- | --- | --- |
| Solubility in Water w/v | 33% | 1.5% | <0.1% |
| Quantity 1st Coating w/w | 10–11% | 4–5% | 2–3% |

The present invention is described further in specific working examples that are intended to describe the invention without limiting its scope.

EXAMPLE 1

Preparation of a Base Granulate Containing an Active Ingredient Very Soluble in Water at Ambient Temperature

| Composition | % by weight |
| --- | --- |
| Diprophylline | 50 |
| Dicalcium Phosphate/Maize starch | 5/35 |
| Polyvinylpyrrolidone Vinyl Acetate | 10 |

In a Diosna P25 high-shear mixer-granulator (Dierk & Sohne, Osnabruck, Germany), four 5-Kg preparations (A, B, C, A*) of the above composition were prepared according to the following procedure: mix the powders in a high-shear mixer-granulator, then wet the mixture by atomizing the granulation fluid (in this case, water) at steady flow and pressure while the product is subjected to the combined actions of the mixer and mill, until a homogeneous mixture is obtained. Knead for a fixed time, at the end of wetting, still with the combined mixer and mill actions. At the end of kneading the product was dried so as to reach a residual humidity of 5–7%. In the four preparations some of the process parameters shown in Table 1 were changed, whereas others were kept constant (Diagram 1). The preparation designated with an asterisk (*) was purposefully made outside the parameter ranges considered essential to obtain a granulate suitable for coating.

| DIAGRAM 1 | | | | |
| --- | --- | --- | --- | --- |
| Parameter | A | B | C | A* |
| Water (g/Kg of product) | 60 | 120 | 100 | 200 |
| Spray Rate (g/min) | 45 | 25 | 20 | 45 |
| Kneading time (min) | 3 | 8 | 10 | 20 |
| Spray pressure (bars) | 2 (steady) | | | |
| Mixer speed wetting/kneading (rpm) | 175 (steady) | | | |
| Mill speed wetting/kneading (rpm) | 2,000 (steady) | | | |

EXAMPLE 2

Preparation of a Base Granulate Containing an Active Ingredient of Average Solubility in Water at Ambient Temperature

| Composition | % by weight |
| --- | --- |
| Acetaminophen | 80.0 |
| Dibasic calcium phosphate dihydrate | 10.0 |
| Talc | 2.5 |
| Polyvinylpyrrolidone vinyl acetate | 7.5 |

In a Diosna P25 high-shear mixer-granulator, four 3-Kg preparations (D, E, F, D*) of the above composition were prepared according to the procedure described in Example 1.

In the four preparations some of the process parameters shown in Table 1 were changed, whereas others were kept constant (Diagram 2). The preparation designated with an asterisk (,) was purposefully made outside the parameter ranges considered essential to obtain a granulate suitable for coating.

| DIAGRAM 2 | | | | |
| --- | --- | --- | --- | --- |
| Parameter | D | E | F | D* |
| Water (g/Kg of product) | 75 | 120 | 140 | 200 |
| Spray rate (g/min) | 45 | 30 | 25 | 45 |
| Kneading time (min) | 20 | 15 | 10 | 20 |
| Spray pressure (bars) | 2 (steady) | | | |
| Mixer speed wetting (rpm) | 175 (steady) | | | |
| Mixer speed kneading (rpm) | 350 (steady) | | | |
| Mill speed wetting/kneading (rpm) | 4,000 (steady) | | | |

EXAMPLE 3

Preparation of a Base Granulate Containing an Active Ingredient Insoluble in Water at Ambient Temperature

| Composition | % by weight |
| --- | --- |
| Ibuprofen | 80 |
| Lactose | 10 |
| Polyvinylpyrrolidone | 10 |

In a Diosna P25 high-shear mixer-granulator, four 4-Kg preparations (G, H, I, G*) of the above composition were prepared according to the procedure described in Example 1.

In the four preparations some of the process parameters shown in Table 1 were changed, whereas others were kept constant (Diagram 3). The preparation designated with an asterisk (*) was purposefully outside the parameter ranges considered essential to obtain a granulate suitable for coating.

| DIAGRAM 3 | | | | |
| --- | --- | --- | --- | --- |
| Parameter | G | H | I | G* |
| Water (g/Kg of product) | 80 | 150 | 130 | 200 |
| Spray rate (g/min) | 45 | 20 | 25 | 45 |
| Kneading time (min) | 20 | 15 | 10 | 20 |
| Spray pressure (bars) | 2 (steady) | | | |
| Mixer speed wetting (rpm) | 175 (steady) | | | |
| Mixer speed kneading (rpm) | 350 (steady) | | | |
| Mill speed wetting/kneading (rpm) | 2,000 (steady) | | | |

EXAMPLE 4

Physical Tests on a Base Granulate

Nine different preparations (A to I) were tested by determining the following parameters:

D.Ae.: Aerated density; D.Pa.: Packed density; D.Ap.: Apparent density; $d_g$: Mean geometric diameter; $\sigma_g$: Geometric standard deviation; R.A.: Angle of repose; C.I.: Carr index; FL.:Flowability ((I)=inadequate, (A)=adequate, (G)= good).

Preparations (A, B, C), containing a very soluble product, were prepared as described in Example 1; preparations (D, E, F), containing a product of medium solubility, and (G, H, I), containing an insoluble product, were prepared as described in Examples 2 and 3 respectively.

The results are described in Table 6:

TABLE 6

|   | D.Ae. (g/ml) | D.Pa. (g/ml) | D.Ap. (g/ml) | dg (μm) | σg | R.A. ° | C.I. % | FL |
|---|---|---|---|---|---|---|---|---|
| A | 0.571 | 0.735 | 1.410 | 110.2 | 1.61 | 42°12' | 22 | |
| B | 0.542 | 0.625 | 1.450 | 156.7 | 1.62 | 29°23' | 13 | |
| C | 0.584 | 0.648 | 1.380 | 138.0 | 1.58 | 28°34' | 10 | |
| D | 0.598 | 0.724 | 1.427 | 102.5 | 1.57 | 38°35' | 17 | (I) |
| E | 0.596 | 0.684 | 1.429 | 138.7 | 1.50 | 29°24' | 13 | (A) |
| F | 0.628 | 0.695 | 1.429 | 132.0 | 1.55 | 27°46' | 10 | (G) |
| G | 0.513 | 0.625 | 1.200 | 183.0 | 1.44 | 38°46' | 17 | (I) |
| H | 0.513 | 0.576 | 1.220 | 179.2 | 1.44 | 35°23' | 11 | (A) |
| I | 0.536 | 0.580 | 1.280 | 177.7 | 1.42 | 30°34' | 8 | (G) |

Granulates A, D and G present some characteristics which are at the limit of the optimum values shown in Table 4. In particular, the Carr Index and the Angle of Repose are indicative of a rather uneven surface. For granulates B, C, E, F, H, I, by contrast, all the parameters fall within the ranges of Table 4; furthermore, at least two of the parameters (including the Carr Index or the Angle of Repose, which are obligatory) fall within the preferred values of Table 4. It should be noted that corresponding values are not shown for the preparations obtained by operating outside the ranges encompassed by the present invention (designated with asterisks). The material in these preparations was always not of smooth surface, with 85–90% of the particle size distribution over 350 μm and with a mean diameter of 550 μm. Furthermore, in all of these preparations, granule break-up was evident, causing a considerable loss of workable material.

EXAMPLE 5

Granulate Coating

In order to test the granulate suitability for coating, the granulates prepared as described in Example 1 were coated using a Wurster Glatt GPCG3 apparatus with two successive coatings having the following compositions:

|  | Composition | % |
|---|---|---|
| First coating | Ethyl cellulose | 3.0 |
|  | Diethyl phthalate | 1.0 |
|  | Polyethylene glycol | 0.1 |
|  | Chloroform | 74.0 |
|  | Ethanol | 21.9 |
| Second coating | Cellulose acetate phthalate | 4.6 |
|  | Diethyl phthalate | 1.1 |
|  | Acetone | 70.7 |
|  | Isopropanol | 23.6 |

The central partition in the apparatus is set at a height of 8 mm and fitted with a spray nozzle with a 1.2 mm diameter.

The incoming air temperature is set at 45° C. and the air flow is set at 50 m³/hour. The apparatus is switched on when the outgoing air temperature reaches 30° C., the product is then fed and the coating solution is sprayed at a 2 bar pressure and a 20–24 g/min flow rate.

At the end the product is allowed to dry in a fluid motion at 45° C. for 5 minutes.

Two coatings are sufficient to test the granulate suitability for coating. Obviously, if necessary or desirable, a further series of different coatings may be superimposed on the first two. In this experiment, the first coating was in a 2.2:1 ratio with the second coating. It should be noted that the coating is used only as a test for determining how suitable for coating the microgranules are.

The amounts (g) of granules are set forth in the first column of the table herein below. These amounts are obtained from the SA values calculated according to the formulas described above and the values of Table 6.

The corresponding amounts (g) of the first coating are also reported as well as the w/w coating/granulate percentages (in brackets).

| Total Surface Area: 29–31 m² | | |
|---|---|---|
| Granulate g | Coating film g | Coating film w/w % |
| A 700 | 100 | (12.5) |
| B 1000 | 100 | (9.0) |
| C 850 | 100 | (10.5) |
| D 650 | 40 | (5.8) |
| E 900 | 40 | (4.2) |
| F 850 | 40 | (4.5) |
| G 1000 | 25 | (2.43) |
| H 1000 | 25 | (2.43) |
| I 1000 | 25 | (2.43) |

EXAMPLE 6

Evaluation of Dissolution Profiles

The dissolution profiles of the granulates coated as described in Example 5 were tested according to the method provided in USP XXII, apparatus 2 (paddle), under the following operating conditions: temperature=37° C.; rotating speed=50 rpm; dissolution medium 0.1N HCl for the first hour, then phosphate buffer pH=7.5 from the 2nd to the 8th hour. Table 7 shows the release profiles of the coated granulates prepared as described in the preceding examples.

TABLE 7

| 1% Active Ingredient Released | | | | | | | | | |
|---|---|---|---|---|---|---|---|---|---|
| | Diprophylline | | | Acetaminophen | | | Ibuprofen | | |
| Hour | A | B | C | D | E | F | G | H | I |
| 1 | 39.6 | 5.8 | 4.0 | 35.4 | 20.3 | 21.9 | 49.0 | 36.0 | 14.3 |
| 2 | 66.8 | 43.7 | 22.3 | 67.3 | 43.6 | 40.9 | 68.0 | 40.2 | 23.2 |
| 4 | 89.6 | 73.2 | 38.7 | 83.9 | 64.9 | 58.5 | 82.2 | 50.3 | 36.2 |
| 8 | 98.0 | 88.2 | 59.8 | 97.6 | 85.5 | 74.3 | 97.4 | 62.5 | 54.6 |

As a granulate acceptance criterion, with respect to suitability for coating, release of the active ingredient should not exceed a limit of 50% within the first two hours of performance of the dissolution test, but at least 33% should be released within 4 hours.

The release profiles of granulates A, D and G confirmed that they are not suitable for coating, as predicted from the relevant Carr Index and Angle of repose values (Table 6). The granulate surface roughness leads to excessive product release during the first two hours of dissolution.

Granulates B, E and H showed adequate flowability, together with a Angle of Repose value within the preferred limits (Tables 2, 3, 6). The release profile shows that less than 50% of the active ingredient contained in the granules is released in the first two hours.

Granulates C, F and I, which showed Angle of Repose and Carr Index values both within the optimum values, permit an even better modulation of the coating quantity to achieve the required release profile. In other words, their optimum surface characteristics (as indicated by the parametric values) permit a more uniform and efficient coating.

EXAMPLE 7

Superficial Morphological Characteristics of the Granulate

FIGS. 1–4 display the surface characteristics of four different microgranulate preparations:

FIG. 1: Microgranules with uneven shapes and surfaces, corresponding to preparation A in Example 1.

(Image taken with a 33×stereomicroscope.)

Figure 2:
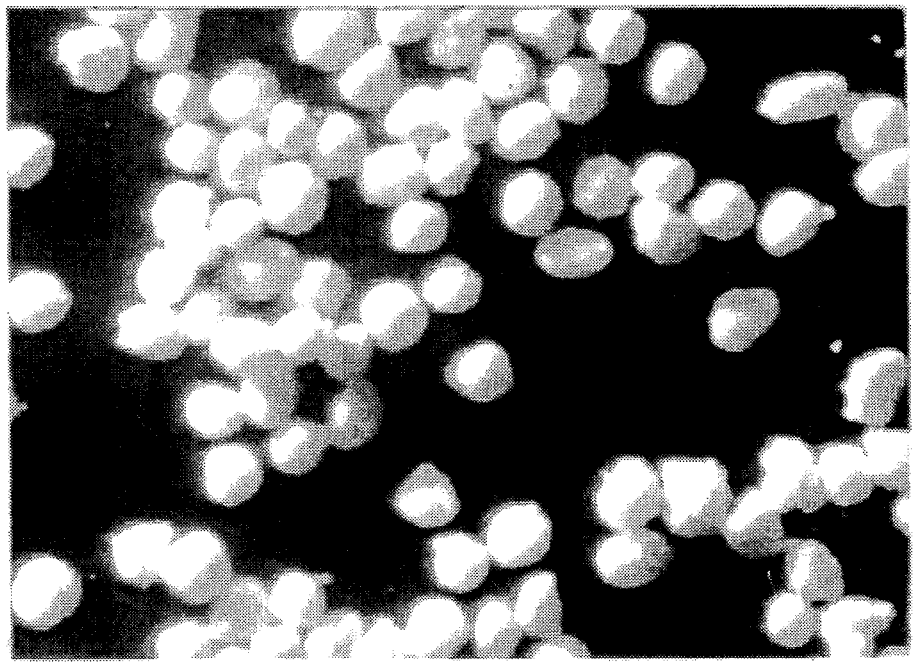
FIG. 2 shows a stereomicroscope image of microgranules with spheroidal shapes and even surfaces, corresponding to preparation C in Example 1. (Magnification=33X).

FIG. 2: Microgranules with even shapes and surfaces, corresponding to preparation C in Example 1.

(Image taken with a 33×stereomicroscope.)

Figure 3:
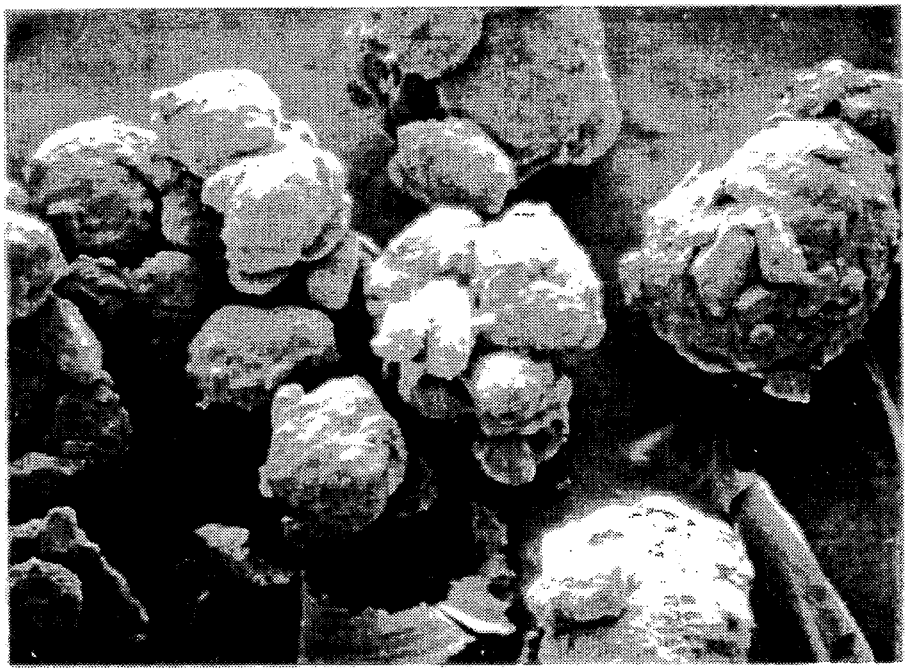
FIG. 3 shows an electron microscope image of microgranules with spheroidal shapes and uneven surfaces, corresponding to preparation G in Example 3.

FIG. 3: Microgranules with spheroidal shapes and uneven surfaces, corresponding to preparation G in Example 3.

(Image taken with a 100×electron microscope.)

Figure 4:
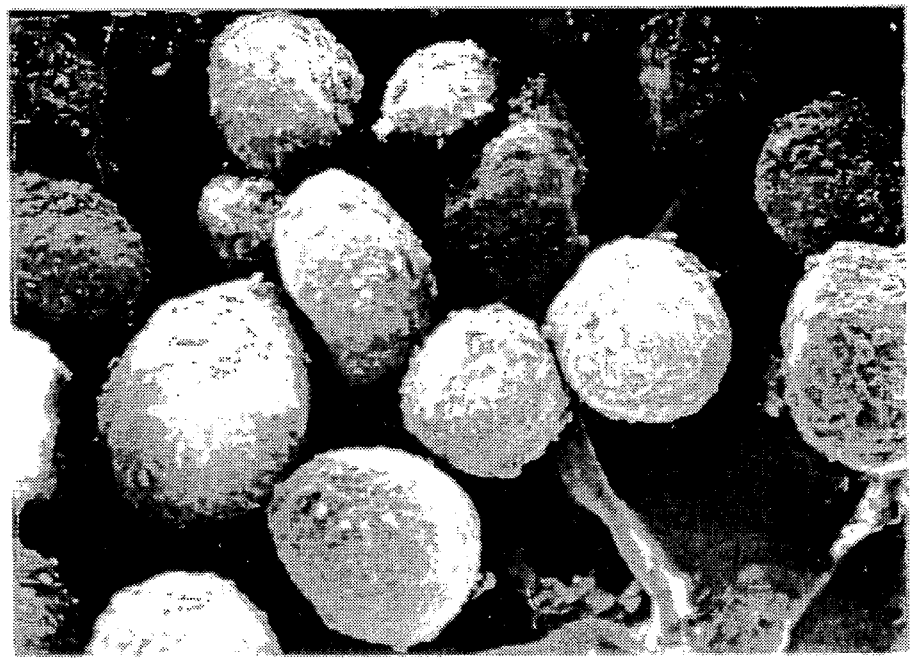
FIG. 4 shows an electron microscope image of microgranules with spheroidal shapes and even surfaces, corresponding to preparation F in Example 2.

FIG. 4: Microgranules with spheroidal shapes and even surfaces, corresponding to preparation F in Example 2.

(Image taken with a 101×electron microscope.)

The images in FIGS. 1–4 completely agree with the considerations reported in Example 4.

What is claimed:

1. A process for the preparation of microgranules suitable for use in controlled-release liquid pharmaceutical formulations, said microgranules having a size smaller than 500 μm, a spheroidal shape and a smooth surface substantially free of roughness, wherein said size, shape, and smooth surface make said microgranules suitable for coating; said process being carried out in a high-shear mixer-granulator for equipped with a mixer and a will, by mixing the active ingredient with excipients, wetting the mixture with 80–180 g granulation fluid per kg mixture, said granulation fluid compromising a member selected from the group consisting of water, organic solvents and mixtures of thereof and being sprayed at a rate of 10–40 g/min, and a pressure of 1.5–2.5 bars, followed by kneading of the mixture for 5–15 minutes using a mixer spell of 175–350 rpm and a mill speed of 2000–4000 rpm.

2. A process according to claim 1, wherein the quantity of said granulation fluid ranges from 100 to 150 grams per kilogram of mixture processed.

3. A process according to claim 1 wherein said spray rate at which said granulation fluid is added to said mixture ranges from 20 to 30 g per minute.

4. A process according to claim 1 wherein said pressure at which said granulation fluid is sprayed onto said mixture is 2 bars.

5. A process according to claim 1 wherein the kneading time used for granulation ranges from 8 to 12 minutes.

6. A process according to claim 1 wherein the mixer rotating speed is 175–350 rpm and the mill rotating speed is 2000–4000 rpm.

7. Microgranules for the controlled release of drugs in liquid suspension obtained by the process according to claim 1, said microgranules, having spheroidal shapes and surfaces suitable for coating, comprising a mean geometric diameter of 120–200 μm with a standard deviation of 1.4–2.0; an aerated density of 0.4–0.7 g/ml; a packed density of 0.5–0.9 g/ml; an apparent density of 1.2–1.5 g/ml; a Carr Index of 5–15% and a angle of repose of 20°–40°.

8. Microgranules according to claim 7, wherein the Carr index is 6–12% and the angle of repose is 26°–30°, and in addition, at least two of the following parameters are within the ranges provided in (a, b, c) below:

(a) mean geometric diameter of 130–170 μm with a standard deviation of 1.5–1.8;

(b) aerated density of 0.50–0.66 g/ml; and (c) packed density of 0.55–0.80 g/ml or apparent density of 1.30–1.45 g/ml.

9. Microgranules suitable for use in control-release pharmaceutical formulations, said microgranules having a size smaller than 500 μm, a spheroidal shape and:

(1) a size distribution wherein at least 55% of said microgranules have a size within the range of about 90 to about 300 μm, with a standard deviation of 1.4–2.0;

(2) a Carr Index within the range of 5–15%;

(3) an angle of repose of 20°–40°;

(4) an aerated density of 0.4–0.7 g/ml;

(5) a packed density of 0.5–0.9 g/ml; and (6) an apparent density of 1.2–1.5 g/ml 10. Microgranules suitable for use in controlled-release pharmaceutical formulations, said microgranules having spheroidal shapes and smooth surfaces, wherein said shapes and surfaces make said microgranules suitable for coating, comprising a mean geometric diameter of 120–200 μm with a standard deviation of 1.4–2.0; an aerated density of 0.4–0.7 g/ml; a packed density of 0.5–0.9 g/ml; an apparent density of 1.2–1.5 g/ml; a Carr Index of 5–15% and a angle of repose of 20°–40°, said microgranules comprising an active ingredient selected from the group consisting of analgesics, antitussives, bronchodilators, antipsychotics, selective β2 agonists, calcium channel blockers, antiparkinson drugs, NSAIDs, antihistamines, antiemetics, antidiarrheal drugs, oral antidiabetic drugs, opioid analgesics, motility stimulants, diuretics, nitrates, β-blockers, antispasmodics, peripheral vasodilators, lipid lowering drugs, antidepressants, laxatives, 4-quinolones, vitamins, antiasthmatic drugs, and antiepileptic drugs.

11. The microgranules of claim 10 wherein said analgesic is acetaminophen.

12. The microgranules of claim 10 wherein said bronchodilator is diprophylline.

13. The microgranules of claim 10 wherein said non-steroid anti-inflammatory drug is ibuprofen.

* * * * *

UNITED STATES PATENT AND TRADEMARK OFFICE
CERTIFICATE OF CORRECTION

PATENT NO. : 5,460,828
DATED : October 24, 1995
INVENTOR(S) : Giancarlo SANTUS, Giuseppe BOTTONI, and Roberto GOLZI It is certified that error appears in the above-indentified patent and that said Letters Patent is hereby corrected as shown below:

Title page, item, [75], Inventors: change "Guiseppe" to --Giuseppe--

Signed and Sealed this

Thirtieth Day of January, 1996

Attest:

BRUCE LEHMAN

*Attesting Officer*  *Commissioner of Patents and Trademarks*